(12) United States Patent
von Borstel et al.

(10) Patent No.: US 8,646,461 B2
(45) Date of Patent: Feb. 11, 2014

(54) DEVICE AND METHOD FOR SIMULATING CHEMOSENSATION OF SMOKING

(71) Applicant: Sentiens, LLC, Charlotte, NC (US)

(72) Inventors: Reid von Borstel, Potomac, MD (US); Dennis Tan, Weddington, NC (US); John Siverling, Matthews, NC (US); Inna S. Timokhina, Potomac, MD (US)

(73) Assignee: Sentiens, LLC, Charlotte, NC (US)

( * ) Notice: Subject to any disclaimer, the term of this patent is extended or adjusted under 35 U.S.C. 154(b) by 0 days.

(21) Appl. No.: 13/710,801

(22) Filed: Dec. 11, 2012

(65) Prior Publication Data

US 2013/0152956 A1    Jun. 20, 2013

Related U.S. Application Data

(60) Provisional application No. 61/570,660, filed on Dec. 14, 2011, provisional application No. 61/651,184, filed on May 24, 2012.

(51) Int. Cl.
*A24F 47/00*    (2006.01)

(52) U.S. Cl.
USPC .......................... 131/273; 131/270; 131/271

(58) Field of Classification Search
None
See application file for complete search history.

(56) References Cited

U.S. PATENT DOCUMENTS

| | | |
|---|---|---|
| 2,342,853 A | 2/1944 | Furstenberg |
| 3,320,953 A | 5/1967 | Rindner |
| 3,521,643 A | 7/1970 | Toth |
| 4,083,372 A | 4/1978 | Boden |
| 4,284,089 A | 8/1981 | Ray |
| 4,429,703 A | 2/1984 | Haber |
| 4,655,229 A | 4/1987 | Sensabaugh, Jr. et al. |
| 4,715,387 A | 12/1987 | Rose |
| 4,765,347 A | 8/1988 | Sensabaugh, Jr. et al. |
| 4,765,348 A | 8/1988 | Honeycutt |
| 4,774,971 A | 10/1988 | Vieten |
| 4,793,366 A | 12/1988 | Hill |
| 4,813,437 A | 3/1989 | Ray |
| 4,907,605 A | 3/1990 | Ray et al. |
| 5,167,242 A | 12/1992 | Turner et al. |
| 5,326,563 A | 7/1994 | Spindler et al. |
| 5,501,236 A | 3/1996 | Hill et al. |
| 5,611,360 A | 3/1997 | Tang |
| 5,666,979 A | 9/1997 | Chase |
| 5,893,371 A | 4/1999 | Rose et al. |
| 6,041,789 A | 3/2000 | Bankert et al. |
| 6,504,048 B1 | 1/2003 | Bachmann et al. |
| 7,614,402 B2 | 11/2009 | Gomes |

(Continued)

FOREIGN PATENT DOCUMENTS

WO    2011117755 A2    9/2011

OTHER PUBLICATIONS

Everaerts, W., et al., "The Capsaicin Receptor TRPV1 is a Crucial Mediator of the Noxious Effects of Mustard Oil," Current Biology 21, pp. 316-321, (Feb. 22, 2011), Elsevier Ltd.

(Continued)

*Primary Examiner* — Michael J Felton
(74) *Attorney, Agent, or Firm* — Baker & McKenzie LLP (57) ABSTRACT

A device for simulating a chemosensation of smoking includes an outer layer, a porous medium and a chemesthetic agent. The porous medium is disposed within the outer layer. The chemesthetic agent is disposed within the porous medium and activates a TRP channel.

26 Claims, 4 Drawing Sheets

(56) References Cited

U.S. PATENT DOCUMENTS

| | | | |
|---|---|---|---|
| 7,766,018 | B2 | 8/2010 | Roth et al. |
| 7,766,019 | B2 | 8/2010 | Luzenberg, Jr. |
| 8,496,950 | B2 * | 7/2013 | Sorge et al. .................. 424/401 |
| 2003/0111088 | A1 | 6/2003 | Fox |
| 2004/0055613 | A1 | 3/2004 | Horian |
| 2004/0256745 | A1 | 12/2004 | Simler |
| 2006/0283468 | A1 | 12/2006 | Lipowicz |
| 2007/0298090 | A1 | 12/2007 | Chen et al. |
| 2008/0241255 | A1 | 10/2008 | Rose et al. |
| 2009/0139533 | A1 | 6/2009 | Park et al. |
| 2012/0042887 | A1 | 2/2012 | Mishra et al. |

OTHER PUBLICATIONS

Trevisani, M., et al., "Ethanol elicits and potentiates nociceptor responses via the vanilloid receptor-1," Nature Neuroscience, vol. 5, No. 6, (Jun. 2002), pp. 546-551.

Westman, E.C., et al., "Airway Sensory Replacement as a Treatment for Smoking Cessation," Drug Development Research, vol. 38, (1996), pp. 257-262.

Westman, E.C., et al., "Airway Sensory Replacement Combined With Nicotine Replacement for Smoking Cessation: A Randomized, Placebo-Controlled Trial Using a Citric Acid Inhaler," Chest, vol. 107, No. 5, (1995), pp. 1358-1364.

Rose, J.E., et al., "Pulmonary Delivery of Nicotine Pyruvate: Sensory and Pharmacokinetic Characteristics," Experimental and Clinical Psychopharmacology, vol. 18, No. 5, (2010), pp. 385-394, 2010 American Psychological Association.

Rowe, D.J., ed., "Chemistry and Technology of Flavors and Fragrances," (2005), Blackwell Publishing Ltd., 351 pages.

Billen, B., et al, "Molecular actions of smoking cessation drugs at $\alpha 4\beta 2$ nicotinic receptors defined in crystal structures of a homologous binding protein," PNAS, vol. 109, No. 23, (Jun. 5, 2012), pp. 9173-9178.

Chung, M-K, et al., "TRPV1 shows dynamic ionic selectivity during agonist stimulation," Nature Neuroscience, vol. 11, No. 5, (May 2008), pp. 555-564.

Chung, M-K., et al., "Cold Suppresses Agonist-induced Activation of TRPV1," J. Dent Res., vol. 90, No. 9, (2011), pp. 1098-1102.

Luisada, A.A., et al., "Alcohol Vapor by Inhalation in the Treatment of Acute Pulmonary Edema," Circulation: Journal of the American Heart Association, vol. 5, (Mar. 1952), pp. 363-369.

Perkins, K.A., et al., "Mood Influences on Acute Smoking Responses Are Independent of Nicotine Intake and Dose Expectancy," Journal of Abnormal Psychology, vol. 117, No. 1, (2008), pp. 79-93.

Riera, C.E., et al., "Compounds from Sichuan and Melegueta peppers activate, covalently and non-covalently, TRPA1 and TRPV1 channels," Research Paper: British Journal of Pharmacology, vol. 157, (2009), pp. 1398-1409.

De Biasi, M., et al., "Reward, Addiction, Withdrawal to Nicotine," Annu. Rev. Neurosci., vol. 34, (2011), pp. 105-130.

Kelley, A.E., "Worms Clear the Smoke Surrounding Nicotine Addiction," Cell, vol. 127, (Nov. 3, 2006), pp. 460-462, Elsevier Inc.

Levin, E.D., et al., "The use of flavor in cigarette substitutes," Drug and Alcohol Dependence, vol. 26, No. 2, (1990), pp. 155-160, Elsevier Scientific Publishers Ireland Ltd.

Okumura, Y, et al., "Activation of TRPV1 and TRPA1 by Black Pepper Components," Biosci. Biotechnol. Biochem., vol. 74, No. 5, (2010), pp. 1068-1072.

Oliveira-Maia, A.J., et al., "Nicotine activates TRPM5-dependent and independent taste pathways," Proc. Natl. Acad. Sci. (Feb. 3, 2009), vol. 106, No. 5, pp. 1596-1601.

Rose, J.E., et al., "Inhalation of vapor from black pepper extract reduces smoking withdrawal symptoms," Drug and Alcohol Dependence, vol. 34, No. 3, (1994), pp. 225-229.

Rose, J.E., et al., "Citric acid aerosol as a potential smoking cessation aid," Chest, vol. 92, No. 6, (1987), pp. 1005-1008.

Rose, J.E., et al., "Blockade of Smoking Satisfaction Using the Peripheral Nicotinic Antagonist Trimethaphan," Pharmacol. Biochem. Behav., (Jan. 1999), vol. 62, No. 1, 30 pages.

Rose, J.E., "Nicotine and nonnicotine factors in cigarette addiction," Psychopharmacology, vol. 184, No. 3-4, (2006), pp. 274-285.

Thuerauf, N., et al., "The Influence of Mecamylamine on Trigeminal and Olfactory Chemoreception of Nicotine," Neuropsychopharmacology, vol. 31, No. 2, (2006), pp. 450-461.

Talavera, K., et al., "Nicotine activates the chemosensory cation channel TRPA1," Nature Neuroscience, vol. 12, No. 10, (Oct. 2009), pp. 1293-1300.

Venkatachalam, K., et al., "TRP Channels," Annu. Rev. Biochem., (2007), vol. 76, pp. 387-417.

International Search Report and Written Opinion of the International Searching Authority, PCT/US2012/069214, dated Feb. 20, 2013, 11 pages.

* cited by examiner

DEVICE AND METHOD FOR SIMULATING CHEMOSENSATION OF SMOKING

CROSS-REFERENCE TO RELATED APPLICATIONS

This application claims priority to U.S. Provisional App. Ser. No. 61/570,660, filed Dec. 14, 2011 and U.S. Provisional App. Ser. No. 61/651,184, filed May 24, 2012, each of which is hereby incorporated by reference in its entirety.

BACKGROUND

Smoking is prohibited in many locations where smokers may spend considerable time, including work places, restaurants, airplanes, and hospitals. In such settings, the experience of craving for cigarettes can cause significant discomfort and distraction. Nicotine absorption into the bloodstream and brain is a factor, but it is not the only or primary factor for relief of cigarette craving, as indicated, for example, by the failure of transdermal nicotine delivery patches or other nicotine replacement therapies to have a dramatic effect on smoking cessation success rates. Nicotine-free cigarettes can reduce cigarette craving symptoms, but they do not represent an alternative for use in environments where smoking is prohibited. It has been suggested that sensory effects of smoke inhalation, and to some extent, the simple motor effects of smoking behavior, may help to alleviate craving.

Habituation to tactile and kinesthetic aspects of handling and smoking a cigarette contributes to reinforcement of smoking behavior, as do the organoleptic qualities of cigarette smoke, the taste and other sensations in the mouth, throat and respiratory tract. Sensory aspects of smoking contribute to smoking behavior and relief of cigarette craving both through conditioned or learned association with nicotine delivery, but also through direct "hard-wired" autonomic and sensory-metabolic reflexes independent of nicotine entry into the brain. In particular, the characteristic airway sensation caused by inhaled tobacco smoke (sometimes referred to as "throat scratch," "throat impact" or "throat hit") is reported as a significant component of smoking satisfaction and especially of relief of acute cigarette craving. Isolated reduction of throat sensations with local anesthetics reduce the relief of smoking craving induced by nicotine-containing cigarette smoke; conversely, maintenance of throat scratch while disabling olfaction and oral taste sensation with an anesthetic mouthwash can alleviate the negative affect associated with cigarette craving. The "throat scratch" can affect perceived taste qualities and more subtle throat and airway autonomic sensory nerve stimulation, which can have effects beyond taste sensations. The airway sensations of inhaled cigarette smoke involve activation of receptors on sensory nerve endings by nicotine, other smoke components, as well as high temperatures of smoke.

An aerosol of citric acid or ascorbic acid has been reported to reduce cigarette craving symptoms via irritation of the throat. However, the airway sensations elicited by aerosols of these nonvolatile acids were accompanied by the sour taste sensations not associated with smoking tobacco and required generation of an aqueous aerosol by using a device that did not resemble a cigarette.

Inhalation of vapor from black pepper oil from a plastic cigarette-like device has been reported to reduce cigarette smoke craving. Some cigarette substitutes that simulate some features of the smoking experience, while acting as non-pyrolytic nicotine delivery devices, have also been described. Other such substitutes have been described which intend to reduce cigarette craving without delivering nicotine. Electrical devices for creating a vapor simulating tobacco smoke have also been described which typically involve heating a solution of nicotine and flavor agents dissolved in propylene glycol or glycerol to produce a smoke-like aerosol that delivers flavorings and nicotine in solvent droplets. Some vaporizing devices are shaped like a cigarette, including a battery, vaporizing chamber and a reservoir for liquid, which can be held in a porous substrate.

However, the devices described above fail to provide a non-combustible, non-electric cigarette substitute that adequately mimics tactile, kinesthetic, organoleptic and/or chemosensory qualities of cigarettes and cigarette smoking for relieving negative affect or mood associated with cigarette craving at times when smoking is not possible or for use in supporting smoking cessation.

BRIEF SUMMARY

In one embodiment, a device for simulating chemosensation of smoking includes an outer layer, a porous medium and a chemesthetic agent. The porous medium is disposed within the outer layer. The chemesthetic agent is disposed within the porous medium and includes a Zingiberaceae extract that activates a TRP (transient receptor potential) channel.

In another embodiment, a device for simulating chemosensation of smoking includes an outer layer, a porous medium and a chemesthetic agent. The porous medium is disposed within the outer layer. The chemesthetic agent is disposed within the porous medium and includes a Brassicaceae extract that activates a TRP channel.

In another embodiment, a device for simulating chemosensation of smoking includes an outer layer, a porous medium and a chemesthetic agent. The porous medium is disposed within the outer layer. The chemesthetic agent is disposed within the porous medium and includes a Lamiaceae extract that activates a TRP channel.

In another embodiment, a device for simulating chemosensation of smoking includes an outer layer, a porous medium and a chemesthetic agent. The porous medium is disposed within the outer layer. The chemesthetic agent is disposed within the porous medium and includes a Toddalioideae extract that activates a TRP channel.

In another embodiment, a device for simulating chemosensation of smoking includes an outer layer, a porous medium and a chemesthetic agent. The porous medium is disposed within the outer layer. The chemesthetic agent is disposed within the porous medium and includes 1'-acetoxychavicol acetate.

In another embodiment, a device for simulating chemosensation of smoking includes an outer layer, a porous medium and a chemesthetic agent. The porous medium is disposed within the outer layer. The chemesthetic agent is disposed within the porous medium and includes 6-paradol.

In another embodiment, a device for simulating chemosensation of smoking includes an outer layer, a porous medium and a chemesthetic agent. The porous medium is disposed within the outer layer. The chemesthetic agent is disposed within the porous medium and includes an isothiocyanate.

In another embodiment, a device for simulating chemosensation of smoking includes an outer layer, a porous medium and a chemesthetic agent. The porous medium is disposed within the outer layer. The chemesthetic agent is disposed within the porous medium and includes camphor.

In another embodiment, a device for simulating chemosensation of smoking includes an outer layer, a porous medium and a chemesthetic agent. The porous medium is disposed within the outer layer. The chemesthetic agent is disposed within the porous medium and includes thymol.

In another embodiment, a device for simulating chemosensation of smoking includes an outer layer, a porous medium and a chemesthetic agent. The porous medium is disposed within the outer layer. The chemesthetic agent is disposed within the porous medium and includes hydroxy-α-sanshool.

In another embodiment, a device for simulating chemosensation of smoking includes an outer layer, a porous medium and ethanol. The ethanol is disposed within the porous medium. A quantity of the ethanol dispersed within the porous medium is in an amount designed to perceivably activate TRPV1 and elicit chemesthetic sensations.

In still another embodiment, a device for simulating chemosensation of smoking includes an outer layer, a porous medium and a chemesthetic agent. The porous medium is disposed within the outer layer. The chemesthetic agent is disposed within the porous medium and includes a low molecular weight organic acid that activates a TRP channel or other acid-activated ion channel on sensory nerves.

In still another embodiment, a device for simulating chemosensation of smoking includes an outer layer, a porous medium, a first chemesthetic agent and a second chemesthetic agent. The porous medium is disposed within the outer layer. The first chemesthetic agent is disposed within the porous medium and activates a first TRP channel. The second chemesthetic agent is disposed within the porous medium and activates a second TRP channel. The second TRP channel is of a different type than the first TRP channel.

Related methods for manufacturing and using such devices and for simulating chemosensation of smoking are also described.

DETAILED DESCRIPTION

Embodiments described herein relate generally to a device for mimicking features of smoking, such as tactile and kinesthetic features, and/or qualities of smoke, such as organoleptic and chemosensory qualities, involving inhalation of volatile agents activating sensory nerve ion channels, such as transient receptor potential channels and acid-sensitive ion channels, in the respiratory tract. Additional embodiments relate to other types of inhalation devices.

The present disclosure is generally directed to compositions, apparatuses and methods for simulating the chemosensation of smoking. In some embodiments, an apparatus takes the form of a cigarette substitute device for alleviating cigarette craving or supporting smoking cessation. The cigarette substitute device may comprise volatile, synergistic activators of transient receptor potential channels, dispersed in a porous substrate imitating the appearance of a cigarette, and providing mimicry of the tactile, sensory and chemosensory experiences of smoking.

In the following discussion, cigarette smoking is used as a generic and illustrative term to include cigarette, cigar or pipe smoking without loss of generality to smoking in general.

Figure 1:
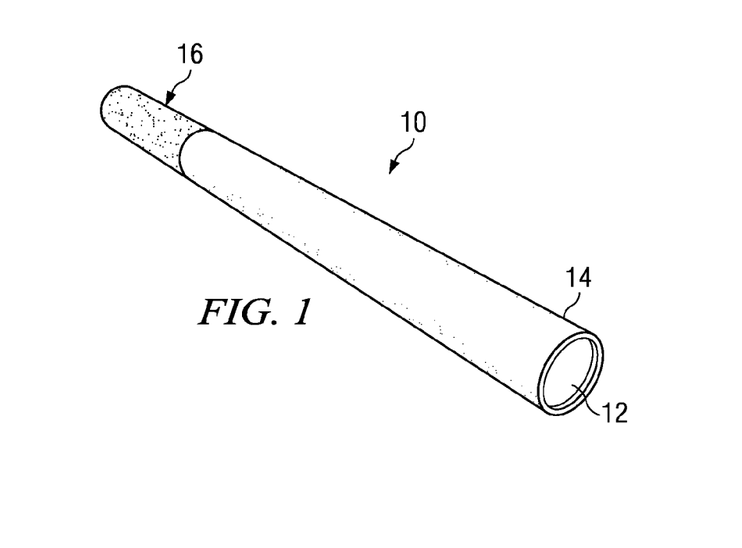
FIG. 1 is a perspective view of an exemplary device for simulating chemosensation of smoking.

Referring to FIG. 1, in some embodiments, improved mimicry of the experience of smoking a cigarette is provided by an exemplary cigarette substitute device 10 approximately the size and shape of a conventional cigarette. Volatile constituents are dispersed within a porous matrix 12 encased within a relatively nonporous, liquid impermeable wrapper 14 resembling the outer wrap paper of a conventional cigarette. The device 10 is effective without use of applied heat or electrical or mechanical energy apart from suction applied by the user's inhalation at an end 16 of the device 10. The end 16 may be constructed to resemble a conventional filter rod in appearance and/or feel. In some embodiments, a filter rod is used at the end 16 of the device 10. The device 10, without heat, electrical power or aerosol generation, uses volatile active constituents, which in turn restrict the amount of material that can be delivered versus generated aerosols or smoke. Thus, cigarette-mimicking activity can be achieved that does not require systemic absorption of nicotine or nicotinomimetic cholinergic receptor-activating compounds. This principle is not restricted to cigarette-like devices, but also includes substitute cigars, pipes, and other devices used to smoke tobacco.

Figure 2:
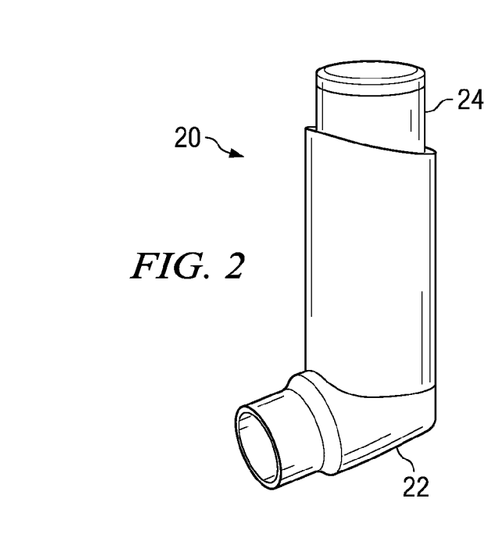
FIG. 2 is a perspective view of an exemplary inhaler device.

The principles of the present disclosure may further be applied to inhaler devices. Referring to FIG. 2, an inhaler device 20 includes a housing 22 and a canister 24. The active constituents are disposed as a solution in the canister 24. When the canister 24 is depressed into the housing 22, a portion of the active constituents are released into the housing 22 in a volatized form. Thus, when the user inhales from the housing 22, the user receives the volatized active constituents.

In one embodiment, compositions of the disclosure are delivered to the airway with an inhaler similar to those used for asthma medications or with a spray device similar to those used for breath fresheners.

Figure 3:
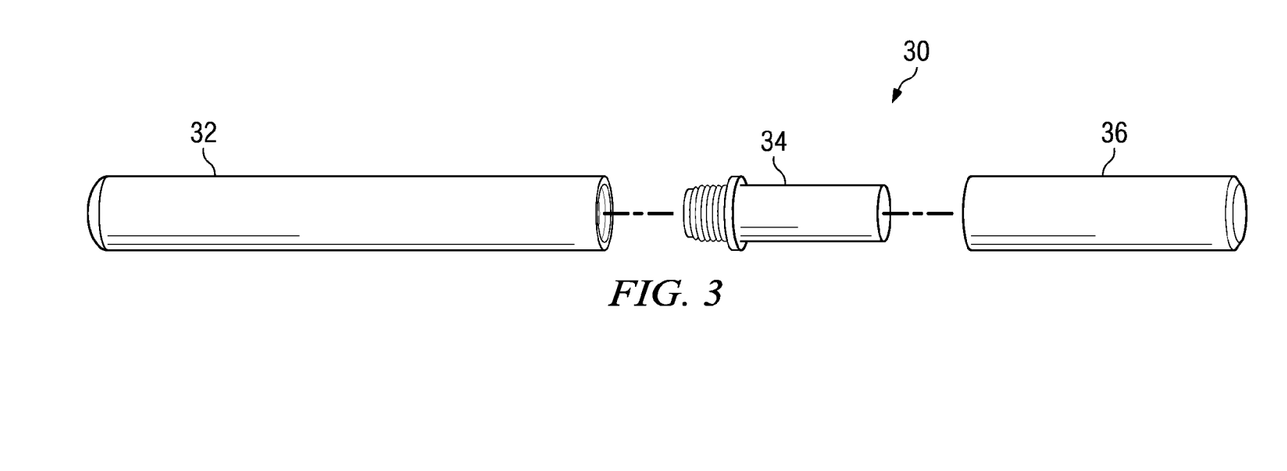
FIG. 3 is an exploded schematic side view of an exemplary device for simulating chemosensation of smoking.

The compositions of the present disclosure are also applicable for use in liquids used in electronic cigarettes or electric vaporizers in conjunction with either an absence or reduced levels of nicotine to provide an adequate simulation of the chemosensory experience of inhaling aerosols containing nicotine as an aid to reducing dependence upon, or craving for, nicotine. Referring to FIG. 3, an electronic cigarette device 30 includes a battery 32, an atomizer/vaporizer 34 and a cartridge 36. The active constituents are disposed as a solution in the cartridge 36. The atomizer 34 uses energy from the battery 32 to volatize the active constituents, which are then delivered to a user inhaling from an end of the device 30.

Devices and methods of this disclosure can also be used to deliver tobacco extracts including nicotine, alone or in combination with chemosensory TRP receptor activators. In one embodiment, nicotine is included in an ethanolic extract and disposed within a porous substrate in cigarette-like rod, such that inhalation on the rod aerosolizes, nebulizes or volatilizes sufficient nicotine to provide acute relief of cigarette craving in a tobacco smoker, but without combustion of tobacco or application of heat. Over time the nicotine content of devices can be progressively reduced in the course of a cessation program to provide weaning from nicotine dependence with chemosensory agents of the disclosure replacing the airway sensation of nicotine as the actual nicotine delivery is diminished.

Chemosensory cigarette-mimetic devices and compositions of the disclosure may also optionally used in conjunction with other forms of nicotine replacement therapy, including but not limited to nicotine-containing dermal patches, gums, lozenges, aerosols, electronic cigarettes or smokeless tobacco products. In this situation, combined delivery of nicotine, along with use of devices and compositions of this disclosure to provide chemosensory and tactile mimicry of a cigarette, may assist in withdrawal from cigarette smoking.

An understanding of actions of nicotine that permit improvements in mimicry of its subjective and physiological effects in a non-combustible simulated cigarette is that its initial perceived actions are upon sensory nerves in the respiratory tract. Cigarette smoke constituents, including but not limited to nicotine, act on sensory and autonomic afferent nerve terminals sending sensory information to the brain from the mouth, throat and respiratory tract via the vagus, trigeminal and other cranial nerves, and induce autonomic reflexes and effects in the central nervous system that contribute to the subjective experience of cigarette smoking, including "throat scratch," and to relief of craving, and also to subjective reflex-mediated experiences such as "head rush." Cigarette smoking causes EEG changes and corresponding subjective experiences in the brain via sensory reflexes even before nicotine is absorbed and transported to the brain.

The pharmacological actions of nicotine include mediation through nicotinic cholinergic receptors in the central and peripheral nervous systems. According to principles of the present disclosure, a class of chemosensory receptors, pharmacologically and physiologically distinct from nicotine-responsive cholinergic receptors can be exploited by compositions and devices disclosed herein to provide mimicry of the sensation of inhalation of cigarette smoke to a degree sufficient to provide satisfaction and attenuation of craving for nicotine-containing cigarettes without requiring the use of nicotine or nicotinic cholinergic receptor agonists, which are generally toxic or malodorous. Simulation of sensations elicited by inhaled cigarette smoke on nerve endings in the respiratory tract is achieved with selected volatile agents acting on the chemesthetic sensory modality mediated by transient receptor potential channels ("TRP channels" or, simply "TRP"), which are pharmacologically distinct from nicotine-responsive cholinergic or acetylcholine receptors.

The chemical senses comprise taste, olfaction, and "chemesthesis" (also known as the "common chemical sense," or trigeminal chemosensation). Chemesthesis refers to actions of chemicals, e.g. food constituents, on nerve endings mediating sensations of pain or temperature, including the pungent, hot or cool sensations elicited by specific constituents of many ingested or inhaled substances including hot peppers (capsaicin), black pepper (piperine), menthol, garlic (allicin), horseradish and wasabi (allyl isothiocyanate), camphor, wintergreen, cinnamon (cinnamaldehyde), carbonated beverages (carbon dioxide) and some air pollutants. Such sensations in the oral and nasal cavities are mediated via the trigeminal nerve, and are elements of the somatosensory system, distinguishing them from olfaction and taste, although chemesthesis is an integral component of characteristic sensory information about foods or airborne chemicals. In the throat, respiratory tract and lungs, chemesthetic signals are transmitted to the brain via the glossopharyngeal and vagus nerves. Chemesthetic signals can thereby directly affect brain activity in the somatosensory cortex and other brain regions, including appetitive circuits involved in craving for particular foods or other chemesthetic stimuli including tobacco smoke, without requiring absorption of the active agents into the bloodstream or the brain. Crossover of chemesthetic signaling provided by compounds of the present disclosure with chemesthetic signaling pathways involved in perception and physiological responses to tobacco smoke contributes to the ability of devices and compositions of the present disclosure to reduce craving or negative affect or mood associated with delay or withdrawal of tobacco smoke. During tobacco smoking, chemosensory signals from the respiratory tract inform the brain that smoke, likely containing nicotine based on experience, has been inhaled, thereby triggering alterations of activity in appetitive circuits involved in converting absence of central nicotinic receptor activation into negative affect or dysphoria associated with cigarette craving. Activation of chemosensory neurons that anatomically or functionally overlap with neurons terminating in the airways that respond to nicotine and other smoke constituents provides signals to the brain that similarly trigger neural reflex-mediated relief of nicotine-withdrawal dysphoria without actually delivering nicotine or potentially toxic smoke constituents resulting from combustion of tobacco. Similarly, mimicry of tactile, kinesthetic, organoleptic aspects of cigarette smoking, in addition to chemosensory mimicry, reinforces the ability of devices and compositions of the present disclosure to relieve symptoms of nicotine withdrawal or cigarette craving.

Transient receptor potential ion channels are a class of receptors on sensory nerves that trigger chemesthetic nerve activation. TRP channels mediate pungent, hot or cool sensations of food or air constituents. TRP activation on sensory nerve endings can induce local effects in addition to sensation per se (e.g. focal vasodilatation via axon reflex) or may trigger sensory-autonomic reflexes (e.g. changes in bronchial tone, coughing, sneezing or changes in body temperature regulation, or subjective sensations) mediated through the reflex arcs involving the spinal cord or brain. While TRP activation can provide warning of potentially noxious environmental or dietary factors, TRP stimulation can also elicit pleasure or satisfaction, as is implied by the examples of common TRP activators above. A feature of TRP activation is that chemesthetic sensations (or TRP sensations), which are generally more sensitive to temperature sensations than to smell sensations provide less inherent discrimination between different agonists than is the case for olfactory sensation. Sensory nerve endings associated with the trigeminal, glossopharyngeal and vagus nerves may contain multiple types of chemosensory receptors, providing a basis for chemesthetic mimicry by chemically diverse agents.

TRP channels can be activated by concentrations of compounds below those that cause actual physical changes in the respiratory tract, acting as sensitive sentinels of possible irritation or damage. TRP channel activators therefore provide a potential mode of action for volatile constituents to have smoke-mimetic chemosensory or chemesthetic effects without delivery of otherwise bioactive quantities of the sensory agents into the body.

In some embodiments, a defined selection of volatile activators of TRP channels and acid sensitive ion channels is provided that, when incorporated into a cigarette-simulating device, provide improved chemosensory mimicry of the experience of smoking a cigarette versus prior art cigarette substitute devices.

In an exemplary cigarette substitute device, such as device 10, synergistic activity of combinations of TRP activators and modulators elicit a chemesthetic sensation. TRPV1, for example, is a temperature-sensing TRP channel. Ethanol reduces the threshold for activation of TRPV1 by heat and by TRPV1 agonists, such as extracts of Szechuan pepper or mustard seeds. This is the basis for a warm sensation in the mouth and throat elicited by beverages containing ethanol;

TRPV1 is activated at body temperature in the presence of ethanol, whereas higher temperatures are normally needed to create sensations of warmth and heat. Acid extracellular conditions, for example with a pH below about 6, also sensitize TRPV1 to other agonists and modulators, including ethanol. TRPA1, a member of the TRP family mediating heat sensations, is sensitized to its agonists by acidic intracellular pH conditions. Simultaneous sensitization of TRPV1 and TRPA1 can thus be achieved by exposure of cells to low molecular weight organic acids that can readily traverse cell membranes, preferably acids that do not have a distinctive or unmaskable odor in quantities sufficient for contributing to chemosensory mimicry of cigarette smoke. Preferred low molecular weight organic acids of this disclosure are carboxylic acids with three or fewer carbon atoms, comprising only carbon, oxygen and hydrogen. Suitable low molecular weight organic acids contemplated herein include pyruvic acid and propionic acid.

Synergistic interaction of TRP channel agonists and modulators provides a unique basis for chemosensory mimicry of inhaled cigarette smoke achieved with limited quantities of material that can be volatilized from a porous matrix within a device approximately the size and shape of a cigarette via mouth-applied suction, without heat or combustion.

An embodiment according to the present disclosure includes ethanol, optionally one or more volatile agonists of TRPA1, TRPV1, TRPV3, or TRPM8, optionally a volatile low molecular weight carboxylic acid, and optionally flavor and aroma agents. Another embodiment according to the present disclosure includes ethanol, one or more volatile agonists of TRPA1, TRPV1, TRPV3, or TRPM8, and optionally flavor and aroma agents. This composition is applied to a porous matrix, such as cellulosic fibers, within an impermeable wrapper resembling the outer wrap paper of a cigarette, such as paper coated with an impermeable ethanol-resistant film or layer. Mouth suction applied to the end of the porous matrix volatilizes the constituents such that they contact the mouth, respiratory tract, and nasal cavity and interact to elicit organoleptic and chemesthetic imitation of the sensory effects of inhaled cigarette smoke sufficient to alleviate discomfort or negative affect associated with cigarette craving.

Preferably, a TRP channel activator provides subjective and physiological mimicry of the chemosensory experience of cigarette smoking without also providing obvious sensory cues attributable to familiar, recognizable food-derived chemesthetic agents such as the TRP activating components of black pepper, red pepper, garlic, horseradish, cinnamon, wintergreen, mint and the like, or common recognizable food acids such as acetic or citric acid. In some embodiments a complex mixture of different TRP activators is formulated, which reduces individual smell and taste attributes and increases the chemosensory effects via synergy.

Furthermore, TRP channel activators for use in compositions and devices of this disclosure preferably have rapid rates of onset and disappearance and do not readily desensitize their receptors to repeated stimulation so that perceived sensation intensity disappears rapidly in the interval between puffs and intensity does not rapidly diminish during prolonged or repeated puffing.

TRP activators that may be useful for mimicry of chemosensory effects of tobacco smoke include 6-paradol and analogs (including extracts of *Aframomum Melegueta* seeds), 1'-acetoxychavicol acetate and analogs (including extracts of galangal root and compounds), isothiocyanates and analogs (including extracts of *Brassica Nigra* seeds), camphor and analogs (including extracts of *Rosmarinus Officionalis* leaves), Thymol and analogs (including extracts of *Thymus Serpullum* leaves) and ethanol. TRP activators and organic acids are preferably present in the cigarette substitute device 10 in quantities sufficient to provide distinct pungent or warm sensations in the throat and respiratory tract when inhalation or suction similar to puffing on a cigarette is applied to the tip of the device.

In some embodiments, sufficient quantities of ethanol, disposed in a porous substrate with sufficient surface area and air flow characteristics (for example, 0.1 to 1.5 ml of ethanol disposed in a device similar in size and shape to a cigarette, but comprising a porous matrix capable of retaining liquid ethanol encased in an ethanol-impermeable outer layer), are used to provide a concentration of ethanol vapor in the main airstream sufficient to elicit distinct chemesthetic sensations of heat or burning in the mouth, throat and/or airways during mouth-applied suction, delivering approximately 50 to 100 microliters of vaporized, nebulized or aerosolized ethanol per puff (i.e., an inhalation of an air volume of approximately 25 to 100 ml over a time period of approximately 1 to 5 seconds). This is in contrast with devices used to provide ethanol aerosol or vapor as a means to deliver ethanol and oxygen for hedonic purposes, or for treatment of pulmonary edema, or cigarette-like devices containing incidental ethanol as a solvent, but in quantities and a matrix insufficient to elicit significant chemosensation during ambient temperature inhalation, where the concentration of ethanol achieved in the main airstream is below the threshold for a chemesthetic sensation sufficient for chemosensory mimicry of inhaled tobacco smoke, as this degree of chemesthetic sensation limits continued deep inhalation.

Exemplary Compositions that Include Constituents that Activate One or More Subtype of TRP Channel In the airways, sensory cues associated with smoking a cigarette are complex and include irritation of airways by nicotine and other smoke constituents via receptors on afferent nerves; irritation of airways by toxic components of cigarette smoke, e.g. acrolein (a major constituent of tobacco smoke), via TRPA1 receptor and perception of warmth/heat associated with the process of combustion and inhalation of tobacco smoke, mediated by thermo-sensing TRP receptors, including TRPV1 (hot sensing >42 degrees C.) and TRPV3 (warm sensing 32-39 degrees C.). Compositions of the present disclosure can act on one, two or multiple chemosensory receptors to provide sensory mimicry of cigarette smoke inhalation.

TRP activating agents are categorized based on TRP channel subtypes affected by constituents. Blending of botanical extracts or constituents that activate different TRP channels, or which activate channels with different kinetics of onset, duration, and inactivation can result in a spectrum of variations in sensory effects, altering the dominant locations of perceived sensation (oral cavity, upper airways, lower airways) and autonomic reflexes triggered by the sensory nerve activation.

TRP-activating compounds or combinations thereof may be selected based on performance using sensory evaluation. Following extensive evaluation, it was unexpectedly discovered that an exemplary composition comprising ingredients that activate more than one subtype of TRP channel can intensify the chemosensory experience and/or expand the area of sensations within the oral cavity and airways. This can also enhance autonomic reflexes including but not limited to bronchodilation. Table 1 provides exemplary combinations of TRP activators that may be used in accordance with the present disclosure.

TRP receptor activation by agonists may be determined using electrophysiological methods, such as whole cell patch recordings of agonist evoked currents. Additionally, the agonist evoked currents can be measured as changes in cell membrane potential, and/or changes in intracellular calcium [$Ca^{++}$] levels, using specific fluorescent dyes.

In an exemplary method to determine activation of a specific TRP receptor subtype, e.g. TRPA1, but not TRPV1, a human embryonic kidney 293 (HEK293) cell line, which does not express endogenous TRP receptors, is transiently or stably transfected with specific TRP receptor cDNA. The functionality of such exogenously expressed TRP receptors is then confirmed by functional assays, described above. The findings obtained with HEK293 cells, may be confirmed using cultured neurons, expressing endogenous TRP receptors. Cell systems for such studies may be neurons isolated from Trigeminal ganglia, which can be obtained from rats or other laboratory animals.

TABLE 1

Exemplary constituents that activate TRP channels

| Exemplary Constituents that activate TRPA1 channel | Exemplary Constituents that activate TRPV1 channel | Exemplary Constituents that activate TRPV3 channel |
|---|---|---|
| Eugenol and analogs, and botanical extracts of the Myrtaceae subfamily, comprising Eugenol, including Allspice, *Pimenta Dioica*, Clove, *Syzygium Aromaticum* and others | Ethanol | Camphor and analogs, and botanical extracts, of the Lamiaceae family, comprising Camphor, including extracts of Rosemary leaves, *Rosmarinus Officinalis* and other botanicals |
| 1'-acetoxychavicol and analogs, and botanical extracts of the Zingiberaceae family, comprising 1'-acetoxychavicol, including extracts of Galangal root, *Alpinia Galanga*, related plants and other botanicals | Camphor and analogs, and botanical extracts, of the Lamiaceae family, comprising Camphor, including extracts of Rosemary leaves, *Rosmarinus Officinalis* and other botanicals | Eugenol and analogs, and botanical extracts of the Myrtaceae subfamily, comprising Eugenol, including extracts of Allspice, *Pimenta Dioica*, Clove, *Syzygium Aromaticum* and related plants |
| Isothiocyanates and analogs, and botanical extracts of the Brassicaceae family, comprising glucosinolates and isothiocyanates, including extracts of mustard seeds, *Wasabia Japonica*, *Sinapis Alba*, *Raphanus Sativus*, *Lepidium Sativum*, *Nasturtium Officinale*, *Brassica Juncea*, *Brassica Nigra*, *Armoracia Rusticana* and related plants | Eugenol and analogs, and botanical extracts of the Myrtaceae subfamily, comprising Eugenol, including extracts of Allspice, *Pimenta Dioica*, *Syzygium Aromaticum* and related plants | Thymol and analogs, and botanical extracts of the Lamiaceae family, comprising Thymol, including extracts of Thyme leaves, *Thymus Serpyllum*, and related plants |
| Hydroxy-α-sanshool and analogs, and botanical extracts, comprising Hydroxy-α-sanshool, including extracts of Szechuan Pepper, *Xanthoxylum piperitum*, other botanicals of the Toddalioideae subfamily and other botanicals | Hydroxy-α-sanshool and analogs, and botanical extracts, comprising Hydroxy-α-sanshool, including extracts of Szechuan Pepper, *Xanthoxylum piperitum*, other botanicals of the Toddalioideae subfamily and other botanicals | Vanillin and analogs, and botanical extracts of the Styracaceae family, comprising Vanillin, including extracts of Benzoin resin, Styrax Benzoin and other botanicals |
| 6-paradol and analogs, and botanical extracts of the Zingiberaceae family comprising 6-paradol, including extracts of *Aframomum Melegueta*, other *Aframomum* species and other botanicals | 6-paradol and analogs, and botanical extracts of the Zingiberaceae family comprising 6-paradol, including extracts of *Aframomum Melegueta*, other *Aframomum* species and other botanicals | Other TRPV3 activators |
| Thymol and analogs, and botanical extracts of the Lamiaceae family, comprising Thymol, including extracts of Thyme leaves, *Thymus Serpyllum*, and related plants | Isothiocyanates and analogs, and botanical extracts of the Brassicaceae family, comprising isothiocyanates, including extracts of mustard seeds, of *Wasabia Japonica*, *Sinapis Alba*, *Raphanus Sativus*, *Lepidium Sativum*, *Nasturtium Officinale*, *Brassica Juncea*, *Brassica Nigra*, *Armoracia Rusticana* and related plants | |
| Other TRPA1 activators | Other TRPV1 activators | |

TABLE 2

Constituents that activate TRPM8
Exemplary Constituents that activate TRPM8 channel Menthol and analogs,
and botanical extracts of the Lamiaceae family,
comprising menthol,
including extracts from Peppermint, *Mentha Piperita* and other sources
Citral and analogs,
and botanical extracts, comprising citral,
including extracts from Mandarin orange,
*Citrus Reticulate*, Lemongrass, *Cymbopogon Citratus* and other sources
Citronellal and analogs,
and botanical extracts, comprising citronellal,
including extracts from Lemon, *Citrus Limon*, *Melissa*, *Melissa Officinalis* and other sources
Linalool and analogs,
and botanical extracts, comprising linalool,
including extracts from Bergamot, *Citrus Bergamia*, Lemon, *Citrus Limon*, and other sources
Eucalyptol and analogs,
and botanical extracts, comprising linalool,
including extracts from *Eucalyptus*, *Eucalyptus Polybractea*
Other TRPM8 activators In some embodiments, constituents that activate TRPM8 are used as optional flavor components that activate the cool sensing TRPM8 channel (25-28° C.) in the airways.

In some embodiments, the composition disposed in the device 10 includes a stabilizing or fixative constituent that reduces evaporation rate and improves stability. When added to more volatile components, the stabilizing or fixative constituent allows the formula in the device to last longer while keeping its original intensity. One suitable fixative constituent is *Benzoin* resin. *Benzoin* resin or *styrax* resin is a balsamic resin obtained from the bark of *Styrax Benzoin* and other species of trees in the genus *Styrax*. *Benzoin* resin also contains vanillin, a TRPV3 activator. Other suitable fixatives include extracts of sandalwood, red cedarwood, vetiver, orris root, oakmoss, myrrh and others.

In one embodiment, 0.1 to 1.5 ml of ethanol dispersed in a porous or fibrous insoluble cellulosic substrate encased in a relatively nonpermeable wrapper with dimensions and airflow resistance characteristics (or "draw") approximating those of a cigarette is sufficient to elicit chemesthetic sensations contributing to mimicry of tobacco smoke inhalation. In such a device, 0.1 to 1.0 ml of pyruvic acid, with or without concurrent inhalation of ethanol vapor (either in a parallel channel or in a mixture comprising pyruvic acid and ethanol) is sufficient to elicit chemesthetic sensations contributing to mimicry of tobacco smoke inhalation. Note that the above specified quantities are merely exemplary and accordingly this disclosure is not limited to such specified quantities.

Figure 4:
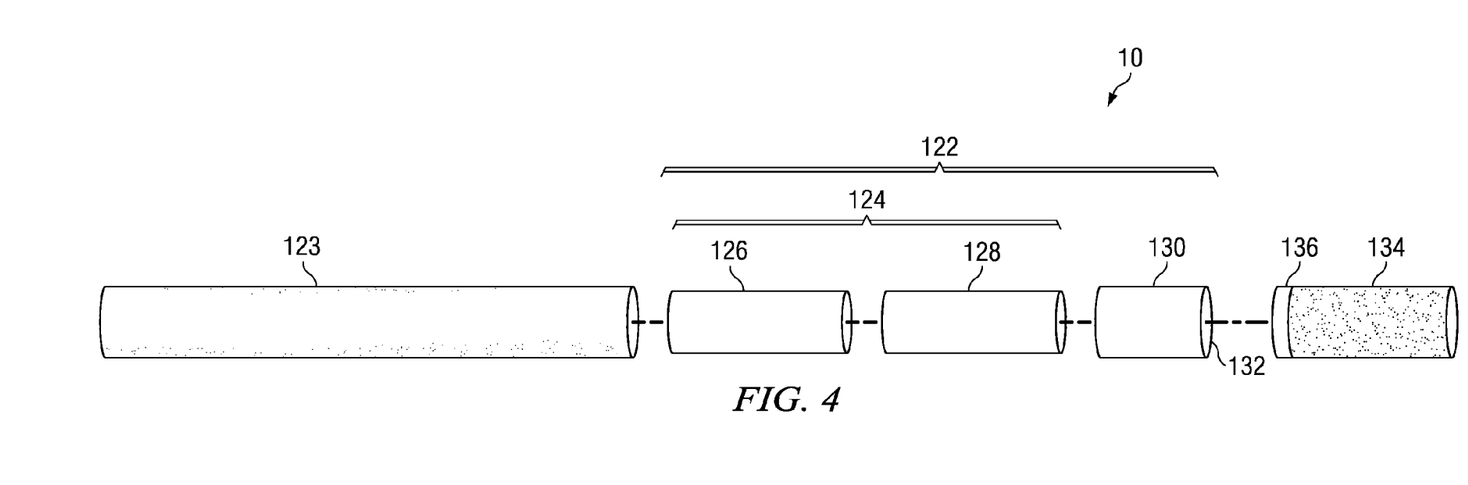
FIG. 4 is an exploded schematic side view of an exemplary embodiment of the device of FIG. 1.

Referring to FIG. 4, an exemplary embodiment of a device 10 includes a porous substrate 122 enclosed in a nonporous wrapper 123 resembling the outer wrap of a cigarette. The porous substrate 122 may include a single lumen or channel 124, or alternatively a double lumen separating the channel 124 into a first region 126 and a second region 128, each comprising a porous substrate encased within a nonporous wrapper, both enclosed within the outer wrapper. The double lumen structure provides for separation of volatile constituents that may adversely affect stability if present together during storage or use. For example, one lumen (e.g., 128) may comprise pyruvic or propionic acid, or a mixture of pyruvic or propionic acid and ethanol, dispersed in a porous substrate, and the other lumen (e.g., 126) may comprise TRP channel activators, tobacco-like flavor and aroma constituents, generally dissolved in ethanol and dispersed in a porous substrate. The lumens 126 and 128 may be arranged with a first porous substrate near a first end of the device 10 and a second porous substrate adjacent to the first porous substrate and distal from the first end of the device 10. Alternatively, the lumens 126 and 128 may extend for a similar length of the device 10 being separated in vertical or horizontal bands. In yet another alternative, the lumens 126 and 128 may be arranged concentrically with a first central porous substrate and a second surrounding porous substrate. The lumens 126 and 128 may be separated by a substantially non-porous or liquid impermeable barrier to provide separation between constituents disposed in the lumens 126 and 128 respectively.

In a single lumen construction, the pyruvic acid and ethanol mixture may be separated from the TRP channel activators by applying the two distinct mixtures in separate alternating bands on the porous substrate with barrier sections between the bands. Additional embodiments having three or more lumens are also contemplated.

An untreated region 130 may be included at a second end 132 of the device 10, which is subjected to mouth-applied suction by a user. The untreated region 130 may be untreated cellulose. In some embodiments, the untreated region 130 may be a filter plug. In some embodiments, the untreated region 130 may be a cellulose acetate tip with a micro capsule (discussed in more detail with respect to FIG. 5).

The region 130 and part of the channel 124 may be covered with a wrap 134. The wrap 134 enhances visual similarity between the device 10 and a cigarette. A portion 136 of the wrap 134 may include trade dress for identifying the device 10 or the maker thereof.

In an embodiment, the device 10 may have a length of approximately 100 mm and a diameter of approximately 7.9 mm in diameter. The channel 124 may be approximately 80 mm in length and the region 30 may be approximately 20 mm in length. The wrap 134 may be approximately 30 mm in length.

Figure 5:
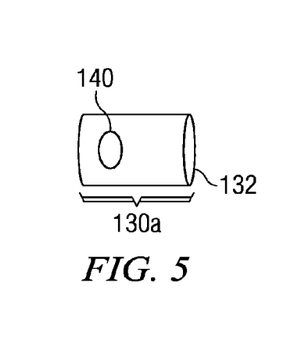
FIG. 5 is a schematic side view of an exemplary cellulose acetate tip of the device of FIG. 1.

Referring to FIG. 5, the region 130a is an exemplary cellulose acetate tip with a micro capsule 140, such as a micro bead. The micro capsule 140 may be of various sizes such as 3.5-5 mm in diameter and may provide for a formula booster containing one or more TRP activating ingredients of the present disclosure or menthol additives. In some embodiments including a micro capsule for a formula booster, the micro capsule may be approximately 5.5 mm in diameter. In some embodiments including a micro capsule for a menthol additive, the micro capsule may be approximately 3.5 mm in diameter. The micro capsule 140 may be arranged with its center at approximately 15 mm from the second end 132.

A preferred porous substrate for high-speed manufacturing is cellulose paper of the type used in manufacturing paper cigarette filter rods on a conventional rod-making machine, though any stable, porous material including but not limited to polypropylene, polyethylene, polyester, or rayon may be used.

A suitable nonporous wrapper for the individual lumens or channels or for the outer wrapper may be conventional outer wrap paper used in cigarette manufacturing, but coated on the inside with a substantially nonporous layer of polyvinylacetate or otherwise laminated with a substantially nonporous flexible plastic material.

An alternate embodiment may utilize a porous substrate material with TRP activators dispersed on the substrate, combined with an acetate cellulose tip that has pyruvic acid, or other constituents disclosed herein, or flavorings agents such as menthol, encapsulated in a preferably 4-5 mm bead positioned in the center of the tip (for example, as shown in FIG. 5).

Another alternative embodiment may combine chemosensory activating ingredients along with stabilizing ingredients in liquefied form, in one embodiment dissolved in propylene glycol or glycerine, for release upon heating from within a cartridge, to be used, for example, in electronic cigarettes or vaporizing devices for generation of a smoke-like aerosol with enhanced chemosensory mimicry of tobacco smoke.

Several variations of device 10 are contemplated herein, including but not limited to single channel configurations comprising ethanol dispersed in a porous substrate, with TRP-active agents or extracts dissolved in the ethanol, e.g.:

1) Cigarette-like rod loaded with an ethanolic extract of a non-tobacco botanical material comprising constituents that activate TRPA1.

2) Cigarette-like rod loaded with a sufficient quantity, such as 0.1 to 1.5 ml, of ethanol to sufficiently activate TRPV1, or to potentiate TRPV1 activation by other agonists, to elicit chemesthetic sensations.

3) Cigarette-like rod loaded with an ethanolic extract of a non-tobacco botanical material comprising constituents that activate TRPV3.

4) Cigarette-like rod loaded with an ethanolic extract of a botanical material comprising constituents that activate TRPA1 and TRPV1.

5) Cigarette-like rod loaded with an ethanolic extract of a botanical material comprising constituents that activate TRPA1 and TRPV3.

6) Cigarette-like rod loaded with an ethanolic extract of a botanical material containing constituents that activate TRPV1 and TRPV3.

7) Cigarette-like rod loaded with an ethanolic extract of a botanical material comprising constituents that activate TRPA1, TRPV1 and TRPV3.

Further embodiments of the device 10 may include two (2) channels, e.g.:

1) a first channel comprising a volatile organic acid dispersed in a porous substrate, with the pH at or lower than the $pK_a$ of the acid; and a second channel comprising a TRPA1 activator dispersed in a porous substrate, optionally as a solution in ethanol.

2) a first channel comprising pyruvic acid dispersed in a porous substrate, optionally a mixture of pyruvic acid and ethanol; and a second channel comprising 6-paradol dispersed in a porous substrate, optionally as a solution in ethanol.

3) a first channel comprising pyruvic acid dispersed in a porous substrate, optionally a mixture of pyruvic acid and ethanol; and a second channel comprising galangal acetate or an analog dispersed in a porous substrate, optionally as a solution in ethanol.

4) a first channel comprising pyruvic acid dispersed in a porous substrate, optionally a mixture of pyruvic acid and ethanol; and a second channel comprising ethanol dispersed in a porous substrate.

The foregoing exemplary composition may be further described with respect to several specific implementations. It is to be appreciated that such specific implementations are exemplary in nature.

Example 1

An extract of *Aframomum Melegueta* seeds was prepared by pulverizing the seeds in an electric coffee grinder and adding three grams of the pulverized seeds to 20 ml of ethanol. After periodic shaking and sitting overnight, 0.4 ml of the ethanolic extract was introduced via a syringe and needle into a cigarette-like rod including crimped porous filter rod paper with a nonporous overwrap. Inhalation from one end of the rod in the manner of someone smoking a cigarette provided a warm chemesthetic sensation mimicking the throat scratch associated with smoking a standard combustible cigarette. The sensation was of greater intensity than that elicited by the equivalent volume of ethanol alone.

Example 2

An extract of galangal root powder was prepared by adding three grams of root powder to 20 ml of ethanol. After periodic shaking and sitting overnight, 0.4 ml of the ethanolic extract was introduced via a syringe and needle into a cigarette-like rod including crimped porous paper with a nonporous overwrap. Inhalation from one end of the rod in the manner of someone smoking a cigarette provided a warm chemesthetic sensation mimicking the throat scratch associated with smoking a standard combustible cigarette. The sensation was of greater intensity than that elicited by the equivalent volume of ethanol alone.

Example 3

Ethanol (0.1 to 1.6 ml by 0.1 or 0.2 ml increments) was introduced via a syringe and needle into a set of cigarette-like rods including crimped porous paper with a nonporous overwrap. Inhalation from one end of the rod in the manner of someone smoking a cigarette provided a warm chemesthetic sensation mimicking the throat scratch associated with smoking a standard combustible cigarette. The intensity of the chemesthetic sensation and its durability with repeated puffing increased dose-dependently.

Example 4

Pyruvic acid (0.1 to 1.0 ml by 0.1 or 0.2 ml increments) was introduced via a syringe and needle into a set of cigarette-like rods including crimped porous paper with a nonporous overwrap. Inhalation from one end of the rod in the manner of someone smoking a cigarette provided a warm chemesthetic sensation mimicking the throat scratch associated with smoking a standard combustible cigarette. The intensity of the chemesthetic sensation and its durability with repeated puffing increased dose-dependently.

Example 5

A 1:1 (v/v) mixture of pyruvic acid and ethanol (0.1 to 1.0 ml by 0.1 or 0.2 ml increments) was introduced via a syringe and needle into a set of cigarette-like rods including crimped porous paper with a nonporous overwrap. Inhalation from one end of the rod in the manner of someone smoking a cigarette provided a warm chemesthetic sensation mimicking the throat scratch associated with smoking a standard combustible cigarette. The intensity of the chemesthetic sensation and its durability with repeated puffing increased dose-dependently. The sensation was more intense than that obtained with equivalent volumes of ethanol alone.

Example 6

A dual lumen cigarette-like device was constructed, including 1) a 3.0 inch long thin-walled polyethylene tube approximately one half of the diameter of a cigarette with its internal lumen filled with crimped filter rod paper; and 2) a 3.25 inch long thin walled polyethylene tube approximately the diameter of a cigarette into which the 3.0 long lower diameter tube was inserted, with the gap between the tubes filled with crimped filter rod paper, thus forming a tube within a tube. Pyruvic acid (0.2 ml) was injected into the inner tube, and ethanol (0.6 ml) was injected into the space between the inner and outer tubes. In separate similarly-constructed devices, ethanol extracts of galangal root powder or pulverized *Aframomum Melegueta* seeds as described in Examples 1 and 2 were used instead of plain ethanol. Mouth-applied suction provided a chemesthetic sensation providing satisfactory mimicry of the chemosensory experience of inhaling tobacco smoke. The addition of tobacco flavoring to the ethanol (or to the corresponding ethanol extract of galangal root or *Aframomum Melegueta* seeds) further enhanced the mimicry of the total olfactory, taste and chemesthetic experience of inhaling tobacco smoke. The outer tube was covered with a cigarette paper overwrap and the tip was covered with the cork paper overwrap of a standard cigarette filter to provide visual mimicry of a cigarette. The exemplary device provides tactile, kinesthetic, olfactory, taste and chemosensory mimicry of a standard cigarette.

Example 7

*Aframomum Melegueta* seeds (3 grams) were pulverized and extracted with 20 ml of 95% ethanol for 1 hour at room temperature. The supernatant was decanted and evaporated to dryness under an air stream. The resultant beige-colored material was dissolved in 10 ml of a nicotine-free electronic cigarette liquid comprising propylene glycol with flavor and fragrance additives. The extract was loaded into an empty electronic cigarette cartridge and affixed to the body of an electronic cigarette, which contained a battery and an airflow-activated switch and provided current to the heating coil within the cartridge element when suction simulating smoking was applied to the opening of the cartridge. The nicotine-free liquid without the extract of *Aframomum Melegueta* seeds provided very little throat or chest sensation characteristic of smoking nicotine-containing cigarettes. The nicotine-free electronic cigarette liquid containing an extract of *Aframomum Melegueta* seeds provided a strong throat and chest sensation simulating that elicited by standard cigarette smoke or electronic cigarette liquid containing nicotine.

Example 8

5 grams of Carbopol 980 polyacrylate was dispersed in 500 ml 95% ethanol in a blender by gradual addition over 10 minutes followed by blending for a further 5 minutes. The Carbopol-ethanol dispersion was stirred overnight on a magnetic stirrer. A 100 ml aliquot was poured into a beaker. 0.1 ml triethanolamine dissolved in 1 ml glycerol was added to the 100 ml portion of the dispersion while stifling continuously. The dispersion became a uniform slightly viscous solution, suitable for mixing with ethanolic extracts of TRP activators and flavor constituents prior to application into cigarette-like rods including a porous matrix encased in a relatively impermeable wrapper. Other carbomer variants and other ethoxylated amine neutralizing agents, preferably with an alkyl or a nonpolar moiety, are optionally used for preparing an ethanolic gel to reduce the rate of evaporation of ethanol and the extent of its seepage in the porous matrix of a device.

Example 9

500 grams of a mixture of powdered *Aframomum Melegueta* seeds, mustard seeds, Szechuan peppercorns and galangal root, rosemary leaves and optionally allspice, in relative percentage ranges as indicated in Examples 10, 11 and 12, was added to an 8 liter cylindrical glass vessel. 2.5 liters of ethanol were added to the vessel, and a concave lid was placed on top and sealed with plastic adhesive tape around the lid joint. The vessel was placed in a double boiler filled with water, and a 2 liter stainless steel canister of ice was placed on top, in the convex lid. The water was heated to 85 degrees C. for 60 minutes. The extract was then allowed to cool to room temperature and filtered through a cloth and a 75 micron nylon mesh. Thymol and *Benzoin* resin were added to the extract in relative percentages as indicated below in Examples 10, 11 and 12 and applied to devices of this disclosure in a volume of 1 ml per rod.

Example 10

Constituents, that activate TRPA1, TRPV1 and TRPV3 channels, listed in Table 1, were obtained as botanical extracts, using a slurry extraction procedure as described in Example 9. The constituents were combined using the ratios listed in Table 3 below.

TABLE 3

Compositions including constituents that activate multiple TRP channels

| Botanical/chemical | Active component | TRP channel | % by weight |
|---|---|---|---|
| Szechuan Pepper | Hydroxy-a-sanshool | TRPA1 TRPV1 | 5-10% |
| Allspice | Eugenol | TRPA1 TRPV1 TRPV3 TRPM8 | 5-10% |
| *Aframomum Melegueta* | 6-paradol | TRPA1 TRPV1 | 15-25% |
| Galangal | 1'-acetoxychavicol | TRPA1 | 30-50% |
| Rosemary | Camphor | TRPV1 TRPV3 | 5-10% |
| Thymol | Thymol | TRPA1 TRPV3 | 0.2-0.4% |
| Mustard seed | Isothionates | TRPA1 TRPV1 | 5-10% |
| Benzoin Resin | Resin, vanillin | TRPV3 | 10-15% |

Figure 6:
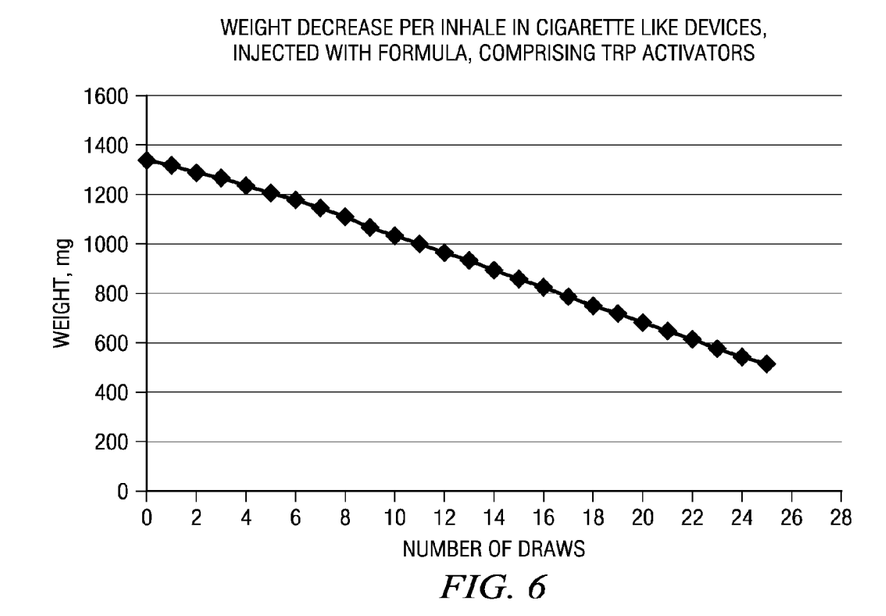
FIG. 6 is a graphical depiction of weight decrease per inhalation in an exemplary embodiment.

The formula from Table 3 (1.5 ml per rod) was introduced via a syringe and needle into a set of cigarette-like rods including crimped porous paper with a nonporous overwrap. Inhalation from one end of the rod in the manner of someone smoking a cigarette provided a chemesthetic sensation of heat/warmth and deep throat scratch mimicking sensations associated with smoking a standard combustible cigarette. The sensation was significantly more intense than that obtained with equivalent volumes of ethanol alone, or any single constituent alone, suggesting synergistic action. As shown in FIG. 6, after each inhale, the weight of cigarette-like rods was measured, revealing that each inhale absorbed 20-40 mg of volatile formula. This configuration of the device permitted at least 25 strong draws, before intensity decreased.

Example 11

Constituents that activate TRPA1, TRPV1 and TRPV3 channels, listed in Table 1, were obtained as botanical extracts using a slurry extraction procedure as described in Example 9. The constituents were combined using the ratios listed in Table 4 below.

TABLE 4

Compositions including constituents that activate multiple TRP channels

| Botanical/chemical | Active component | TRP channel | % by weight |
|---|---|---|---|
| Szechuan Pepper | Hydroxy-a-sanshool | TRPA1 TRPV1 | 15-25% |
| Yellow Mustard | isothiocyanate | TRPA1 | 15-25% |
| Aframomum Melegueta | 6-paradol | TRPA1 TRPV1 | 15-25% |
| Galangal | 1'-acetoxychavicol | TRPA1 | 15-25% |
| Rosemary | Camphor | TRPV1 TRPV3 | 10-15% |
| Thymol | Thymol | TRPA1 TRPV3 | 0.2-0.4% |
| Benzoin Resin | Resin, vanillin | TRPV3 | 10-15% |

The formula from Table 4 (1.5 ml per rod) was introduced via a syringe and needle into a set of cigarette-like rods including crimped porous paper with a nonporous overwrap. Inhalation from one end of the rod in the manner of someone smoking a cigarette provided a chemesthetic sensation of heat/warmth and deep throat scratch mimicking sensations associated with smoking a standard combustible cigarette. The sensation was significantly more intense than that obtained with equivalent volumes of ethanol alone, or any single constituent alone, suggesting synergistic action.

Example 12

Constituents that activate TRPA1, TRPV1 and TRPV3 channels, listed in Table 1, were obtained as botanical extracts, using a slurry extraction procedure as described in Example 9. The constituents were combined using the ratios listed in Table 5 below.

TABLE 5

Compositions including constituents that activate multiple TRP channels

| Botanical/chemical | Active component | TRP channel | % by weight |
|---|---|---|---|
| Szechuan Pepper | Hydroxy-a-sanshool | TRPA1 TRPV1 | 15-25% |
| Yellow Mustard | Benzyl-isothiocyanate | TRPA1 | 5-10% |
| Allspice | Eugenol | TRPA1 TRPV1 TRPV3 TRPM8 | 5-10% |
| Aframomum Melegueta | 6-paradol | TRPA1 TRPV1 | 15-25% |
| Galangal | 1'-acetoxychavicol | TRPA1 | 15-25% |
| Rosemary | Camphor | TRPV1 TRPV3 | 10-15%% |
| Thymol | Thymol | TRPA1 TRPV3 | 0.2-0.4% |
| Benzoin Resin | Resin, vanillin | TRPV3 | 10-15% |

The formula from Table 5 (1.5 ml per rod) was introduced via a syringe and needle into a set of cigarette-like rods including crimped porous paper with a nonporous overwrap. Inhalation from one end of the rod in the manner of someone smoking a cigarette provided a chemesthetic sensation of heat/warmth and deep throat scratch mimicking sensations associated with smoking a standard combustible cigarette. The sensation was significantly more intense than that obtained with equivalent volumes of ethanol alone, or any single constituent alone, suggesting synergistic action.

Example 13

*Benzoin* resin powder (such as that available from bulk herb suppliers) was subjected to the following extraction procedure:

1. Carrier oil (e.g. Canola oil) was incubated in 70° C. water bath for 10 min.
2. 1 part *benzoin* resin was mixed with 1.1 part of pre-warmed carrier oil (weight/volume) and incubated for 1 hour at 70° C. water bath or until fully dissolved, with periodic mixing.
3. The homogenous thick mixture was combined with 2 parts of ethanol and incubated for 1 hour at 70° C., followed by 1 hour at room temperature.
4. Three distinct layers were formed: a layer of resin particles (bottom), a layer of oil (middle), and a layer of sticky ethanol extract (top).
5. The top layer was collected as *Benzoin* resin extract. The extract had a brown color, was slightly viscous, and was highly sticky and aromatic.

Figure 7:
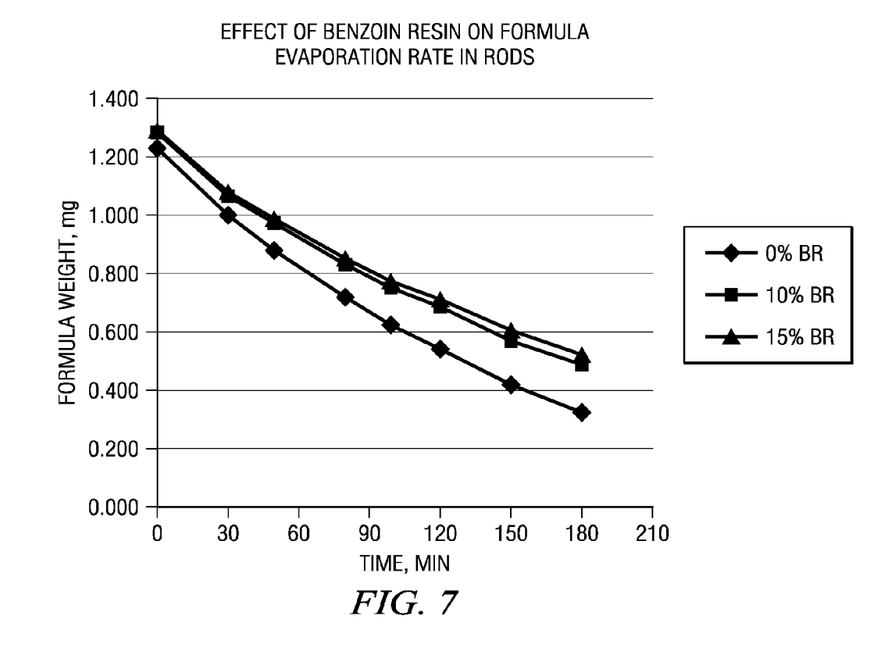
FIG. 7 is a graphical depiction of formula evaporation rate in an exemplary embodiment.

Cigarette-like devices, similar to the ones from Examples 10-12 were injected with 1.5 ml of formula containing 0%, 10% and 15% of *Benzoin* resin extract. As shown in FIG. 7, formula evaporation rate was evaluated by measuring the weight of rods, left unprotected in the open air, over a period of time.

The addition of *Benzoin* resin (BR) significantly reduced formula evaporation rate in cigarette-like rods. The difference between 10% BR and 15% BR (see FIG. 5) was not significant.

Figure 8:
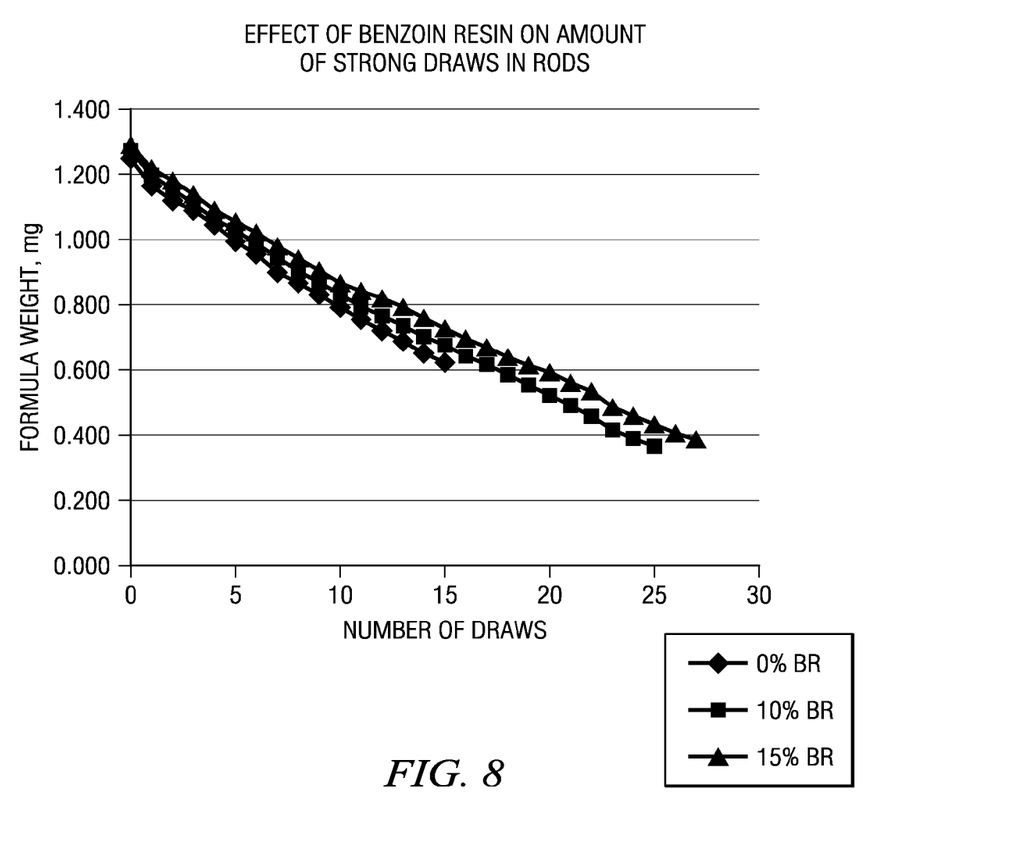
FIG. 8 is a graphical depiction of number of draws per formula weight in an exemplary embodiment.

Cigarette-like devices, similar to the ones from Examples 10-12 were injected with 1.5 ml of formula containing 0%, 10% and 15% of *Benzoin* resin extract. Inhalation from one end of the rod in the manner of someone smoking a cigarette provided a chemesthetic sensation of heat/warmth and deep throat scratch mimicking sensations associated with smoking a standard combustible cigarette. As shown in FIG. 8, after each inhale, the weight of cigarette-like rods was measured and recorded. For each formula, the measurements were conducted until it was determined that the intensity of a chemesthetic sensation of heat/warmth and deep throat scratch started to decrease. The addition of BR increased the number of strong draws in cigarette-like rods from 15 to at least 25.

Example 14

An 8 liter cold-finger extraction apparatus was loaded with 500 ml 95% ethanol. A suspended filter basket contained 100 grams of a powdered plant product TRP source (separately, *Aframomum Melegueta* seeds, galangal root, mustard seeds, or rosemary leaves; additional TRP source materials are extracted similarly) beneath the tip of the ice-chilled cold finger. The apparatus was heated in a 190 degree F. water bath for 6 hours. The resulting ethanolic extract containing active TRP sensation agents can be used as a constituent of ethanolic TRP extracts, optionally also comprising flavoring agents, for loading cigarette-like devices.

Example 15

A mixture of powdered *Aframomum Melegueta* seeds, mustard seeds, Szechuan peppercorns, galangal root, dried rosemary leaves, dried thyme leaves and optionally allspice, in relative percentage ranges as indicated in Examples 10, 11 and 12, were combined with 95% ethanol at 1:1 ratio (w/v) and incubated at room temperature for 30-60 minutes, followed by separation of herbal slurry from the extract, using a French press device. The resulting ethanolic extract containing active TRP sensation agents can be used as a constituent of ethanolic TRP extracts, optionally also comprising flavoring agents, for loading cigarette-like devices.

It will be appreciated that the described exemplary botanical constituents are not limiting and the described chemesthetic agents include equivalents such as synthetic alternatives. It will also be appreciated that description of constituents in compositions as by weight or by volume is merely exemplary and is not limiting. Constituents may be measured using any of a variety of available methods.

In addition, it will be appreciated that the above described devices and compositions are not limited to cigarette-like rods, but are also applicable to other devices such as inhalers that may be used to deliver the volatile constituent(s). Also, it will be appreciated that the above described devices are applicable to applications beyond smoking substitution and smoking cessation.

For example, in addition to providing mimicry of chemosensations similar to tobacco smoke for providing support from smoking cessation or increasing the duration of time free of negative affect between cigarettes, the described devices and compositions are useful for providing sensory cues associated with alcoholic beverages. TRP channel activation by ethanol provides the burning sensation of strong alcoholic beverages that contributes to reinforcement of habitual drinking behavior. Mutations in TRP channels alter alcohol preference behavior in experimental animals. In one embodiment, an alcoholic beverage, such as cognac, whisky, or a liqueur, is diluted with ethanol in a ratio in the range of 0.5:1 to 2:1, and 0.5 to 2.0 ml of the diluted beverage is loaded into a device of the disclosure. Inhalation through the rod results in a strong warm alcohol TRP sensation with minimal actual delivery of ethanol along with the characteristic flavor elements of the particular alcoholic beverage. Alcoholic beverages with a relatively low alcohol concentration such as wine are preferably concentrated by freezing at −20 degrees C. or lower. A portion of the water freezes and the alcohol-containing fraction is poured off and used in a device of this disclosure, optionally after addition of ethanol to further increase volatility. Alternatively, ethanol incorporating concentrated aroma and flavor extracts or components derived from or resembling alcoholic beverages is loaded into a device of this disclosure.

As another example, devices and compositions contemplated herein can also be used for delivery of aromatic agents useful for clearing airways in people with colds, including menthol, camphor, thyme oil, eucalyptus oil or eucalyptol, providing delivery of airway-clearing aromatic agents directly to the throat rather than via nostrils as occurs with nasal tubes or ointments applied around the opening of the nasal passages.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A device for simulating a chemosensation of smoking, comprising:
    an outer layer;
    a porous medium disposed within the outer layer; and
    a chemesthetic agent that activates a TRP channel disposed within the porous medium, the chemesthetic agent including at least one of Zingiberaceae extract, Brassicaceae extract, Toddalioidae extract and Lamiaceae extract;
    wherein the agent is disposed in an ethanol-based solution within the porous medium.

2. The device according to claim 1, wherein the ethanol-based solution includes a stabilizing constituent that includes at least one of a *Benzoin* resin from the Styracaceae family, sandalwood, red cedarwood, vetiver, orris root, oakmoss and myrrh.

3. The device according to claim 1, wherein the TRP channel is a TRP receptor that imparts a chemesthetic sensation.

4. The device according to claim 1, wherein the device is sized and shaped to mimic a cigarette.

5. The device according to claim 1, wherein the agent is a volatile agent.

6. The device according to claim 1, wherein the agent is volatized when suction is applied to the porous medium.

7. The device according to claim 1, wherein the TRP channel is one or more of TRPV1, TRPA1, TRPV3 and TRPM8.

8. The device according to claim 1, wherein the agent includes Zingiberaceae extract.

9. The device according to claim 1, wherein the agent includes Brassicaceae extract.

10. The device according to claim 1, wherein the agent includes Toddalioidae extract.

11. The device according to claim 1, wherein the agent includes Lamiaceae extract.

12. The device according to claim 1, wherein the agent includes at least one of the following:
    approximately 5-10% by weight Szechuan pepper extract, 5-10% by weight mustard seed extract, approximately 5-10% by weight allspice extract, approximately 15-25% by weight *Aframomum Melegueta* extract, approximately 30-50% by weight galangal extract, approximately 5-10% by weight rosemary extract, and approximately 0.2-0.4% by volume thymol solution;
    approximately 15-25% by weight Szechuan pepper extract, approximately 15-25% by weight mustard extract, approximately 15-25% by weight *Aframomum Melegueta* extract, approximately 15-25% by weight galangal extract, approximately 10-15% by weight rosemary extract, and approximately 0.2-0.4% by volume thymol solution; and approximately 15-25% by weight Szechuan pepper extract, approximately 5-10% by weight mustard extract, approximately 5-10% allspice extract, approximately 15-25% by weight *Aframomum Melegueta* extract, approximately 15-25% by weight galangal extract, approximately 10-15% by weight rosemary extract, and approximately 0.2-0.4% by volume thymol solution.

13. The device according to claim 1, wherein the agent includes approximately 10-15% by weight *benzoin* resin extract.

14. A device for simulating a chemosensation of smoking, comprising:
an outer layer;
a porous medium disposed within the outer layer; and
a chemesthetic agent that activates a TRP channel disposed within the porous medium, the chemesthetic agent including at least one of 6-paradol, isothiocyanate, hydroxyl-α-sanshool, 1'-acetoxychavicol, camphor, eugenol and thymol;
wherein the agent is disposed in an ethanol-based solution within the porous medium.

15. The device according to claim 14, wherein the ethanol-based solution includes a stabilizing constituent that includes at least one of a *Benzoin* resin from the Styracaceae family, sandalwood, red cedarwood, vetiver, orris root, oakmoss and myrrh.

16. The device according to claim 14, wherein the agent activates a TRP channel that is a TRP receptor that imparts a chemesthetic sensation.

17. The device according to claim 14, wherein the agent is volatized when suction is applied to the porous medium.

18. The device according to claim 14, wherein the TRP channel is one or more of TRPV1, TRPA1, TRPV3 and TRPM8.

19. The device according to claim 14, wherein the agent includes 6-paradol.

20. The device according to claim 14, wherein the agent includes 1'-acetoxychavicol.

21. The device according to claim 14, wherein the agent includes isothiocyanate.

22. The device according to claim 14, wherein the agent includes hydroxy-α-sanshool.

23. The device according to claim 14, wherein the agent includes camphor.

24. The device according to claim 14, wherein the agent includes thymol.

25. The device according to claim 14, wherein the agent includes at least one of the following:
approximately 5-10% by volume hydroxy-α-sanshool solution, 5-10% by volume isothiocyanates solution, approximately 5-10% by volume eugenol solution, approximately 15-25% by volume 6-paradol solution, approximately 30-50% by volume 1'-acetoxychavicol solution, approximately 5-10% by volume camphor solution, and approximately 0.2-0.4% by volume thymol solution;
approximately 15-25% by volume hydroxy-α-sanshool solution, approximately 15-25% by volume isothiocyanate solution, approximately 15-25% by volume 6-paradol solution, approximately 15-25% by volume 1'-acetoxychavicol solution, approximately 10-15% by volume camphor solution, and approximately 0.2-0.4% by volume thymol solution; and
approximately 15-25% by volume hydroxy-α-sanshool solution, approximately 5-10% by volume isothiocyanate solution, approximately 5-10% by volume eugenol solution, approximately 15-25% by volume 6-paradol solution, approximately 15-25% 1'-acetoxychavicol solution, approximately 10-15% by volume camphor solution, and approximately 0.2-0.4% by volume thymol solution.

26. The device according to claim 14, wherein the agent includes a stabilizing constituent of approximately 5-15% by volume.

* * * * *